US012066363B2

(12) United States Patent
Bicocchi

(10) Patent No.: US 12,066,363 B2
(45) Date of Patent: Aug. 20, 2024

(54) SYSTEM AND METHOD FOR PRESERVING A SURGICALLY EXPLANTED TISSUE SAMPLE

(71) Applicant: Enrico Bicocchi, Leghorn (IT)

(72) Inventor: Enrico Bicocchi, Leghorn (IT)

( * ) Notice: Subject to any disclaimer, the term of this patent is extended or adjusted under 35 U.S.C. 154(b) by 804 days.

(21) Appl. No.: 17/261,538

(22) PCT Filed: Jul. 14, 2019

(86) PCT No.: PCT/IB2019/055995
§ 371 (c)(1),
(2) Date: Jan. 19, 2021

(87) PCT Pub. No.: WO2020/016727
PCT Pub. Date: Jan. 23, 2020

(65) Prior Publication Data
US 2021/0293669 A1   Sep. 23, 2021

(30) Foreign Application Priority Data

Jul. 18, 2018   (IT) .................. 102018000007281

(51) Int. Cl.
*G01N 1/31*     (2006.01)
*A61B 10/00*    (2006.01)
(Continued)

(52) U.S. Cl.
CPC ........... *G01N 1/31* (2013.01); *A61B 10/0096* (2013.01); *B01L 3/502* (2013.01); *B65B 3/003* (2013.01);
(Continued)

(58) Field of Classification Search
CPC ...... G01N 1/31; G01N 1/30; G01N 2001/305; A61B 10/0096; B01L 3/502;
(Continued)

(56) References Cited

U.S. PATENT DOCUMENTS 10,983,034 B2   4/2021   Crum et al.
2009/0105611 A1  4/2009   Wilkinson et al.
(Continued)

FOREIGN PATENT DOCUMENTS

EP           2524595      11/2012
WO      2013043109 A2      3/2013
(Continued)

OTHER PUBLICATIONS

Applicant Bicocchi's Jan. 12, 2022 Submissions to the EPO.†

*Primary Examiner* — Lessanework Seifu
(74) *Attorney, Agent, or Firm* — Reches Patents

(57) ABSTRACT

A system for preserving a surgically explanted tissue sample has a first packing station for placing the tissue sample in a selected container among a plurality of containers of different sizes. Each container has a hermetic lid (50) with an opening (33) equipped with a non-return valve (51). The system also has a final packing station equipped with a filling system for filling the selected container with a preservative substance, including a nozzle-holding head (28) mounted movable on a vertical guide (29). A method is also described which provides for the selection of the container based on the evaluation of the volume of the tissue sample, the hermetic closure of the container immediately after the insertion of the tissue sample. and the filling of the container by means of a nozzle (31) of a filling system inserted in the non-return valve (51) of the hermetic lid (50).

15 Claims, 8 Drawing Sheets

(51) Int. Cl.
  *B01L 3/00* (2006.01)
  *B65B 3/00* (2006.01)
  *B65B 31/04* (2006.01)
  *B65B 55/22* (2006.01)
  *B65B 59/00* (2006.01)
  *G01N 1/30* (2006.01)

(52) U.S. Cl.
  CPC ............ *B65B 31/047* (2013.01); *B65B 55/22* (2013.01); *B65B 59/001* (2019.05); *G01N 1/30* (2013.01); *B01L 2200/026* (2013.01); *B01L 2300/02* (2013.01); *B01L 2300/049* (2013.01); *B65B 2210/04* (2013.01); *G01N 2001/305* (2013.01)

(58) Field of Classification Search
  CPC ........... B01L 2200/026; B01L 2300/02; B01L 2300/049; B01L 2400/0605; B01L 3/00; B65B 3/003; B65B 31/047; B65B 55/22; B65B 59/001; B65B 2210/04; B65B 55/027; B65B 59/003; B65B 31/04; B65D 83/00; A01N 1/0236
  See application file for complete search history.

(56) References Cited

U.S. PATENT DOCUMENTS

| | | |
|---|---|---|
| 2010/0311165 A1 | 12/2010 | Ram |
| 2012/0294782 A1 | 11/2012 | Francesco |
| 2020/0079542 A1† | 3/2020 | Visinoni |

FOREIGN PATENT DOCUMENTS

| | | |
|---|---|---|
| WO | 2016/131859 | 8/2016 |
| WO | 2017/114598 | 7/2017 |
| WO | 2017114598 A1 | 7/2017 |

† cited by third party

SYSTEM AND METHOD FOR PRESERVING A SURGICALLY EXPLANTED TISSUE SAMPLE

TECHNICAL FIELD

The present invention relates to a system and method for preserving a surgically explanted tissue sample.

The system provides a disposable container suitable for containing a tissue sample in a preservative substance, and a machine for introducing said preservative substance into the container itself in conditions of safety for a healthcare professional.

The preservative substance can be a fixative-preservative solution; among the solutions most used, there are those that, since they contain substances known to be toxic by contact and inhalation, must by law be used and transported avoiding risks of exposure of healthcare professionals. Alternatively, the preservative substance can be an inert gas such as nitrogen, or a mixture of inert gases.

BACKGROUND ART

Samples of human or animal tissue or organs or of their parts surgically explanted and to be subjected to diagnostic histopathology examinations, whether histo- and cyto-morphological, or immunohistochemical or molecular must be immersed in a suitable fixative-preservative reagent in order to inhibit degradation processes and maintain intact the architectural and macromolecular structure of tissues.

In health facilities and university clinics, disposable containers of various shapes and capacities are used for this purpose, with a variable volume from 120 ml to 6,500 ml, that are hermetically sealed with a pressure or screw cap, in which a fixative-preservative reagent, typically but not exclusively containing formaldehyde at a con-centration of 2-8% w/v in buffer, is present or added.

The toxicity of formaldehyde, a volatile substance that the updated EU Regulation 605/2014, which integrated the EU Regulation 1272/2008, reclassified formaldehyde as "Carc. 1B"—presumed or certain carcinogenic substance, and as "Muta 2"-substance suspected of causing genetic alterations, has been known from a long time. However, to date, in diagnostic isto-pathology, solutions containing formaldehyde are still considered the best for tissue fixation and preservation.

Therefore, the healthcare professional, on his/her own and others' safety and in compliance with the regulations in force, must use the aforementioned preservative-fixatives as required by the "good laboratory practice", working with great care and adopting all available protective procedures.

US 2012/294782 A1 discloses a method and a system for the automatic dosage of a fixative solution in a flexible plastic bag containing an explant. According to the method described in the aforementioned document, the flexible bag is placed in a dosage device, where the required volume or weight of fixative solution is calculated, based on the mass of the explant or on the volume of the flexible bag containing it. In particular, the flexible bag containing the explant is placed on a balance of the dosing system and, after having introduced the fixative and having removed the air from the inside, it is heat-sealed.

WO2015/092772 A1 describes a thermo-sealing machine for liquid containers after their filling. It comprises a support structure on which a bell element is mounted in a higher position than that of supporting means for at least one container to be filled and sealed. This bell-shaped element comprises a measuring device, die-cutting means and sealing means for die-cutting and sealing a sliding film between said bell-shaped element and the container to be filled.

The supporting means of the container comprises a drawer element, including an opposite recess, suitable for supporting the container.

The machine includes a lifting device for vertically lifting the drawer element and for moving the container from a filling and sealing position to a lower position to allow said film to slide.

The measuring device comprises an injection nozzle, controlled by a metering pump and coupled to a supply tube, coupled in turn to a liquid tank.

US2009191533 A1 describes a process for preserving the tissues which includes the transfer of the tissues into a container and the evacuation of the container.

A vacuum device to preserve tissues after surgery includes a vacuum chamber, a vacuum pump, an electrical control unit, electric valves for air and gas controlling and a thermo-scaler.

WO2017/114598 A1 concerns a machinery and a method for packing, preserving and transporting surgical samples. The sample, placed inside a container, is placed inside the machinery for filling with formalin and subsequent heat-sealing of a pre-treated aluminum disk for sealing said container. At the end of the operation, carried out automatically, an operator closes the container with its rigid lid to be transported safely to the pathological anatomy laboratory.

U.S. Ser. No. 10/109,376 B2 describes a measuring device for tracing tissues comprising a processing area for receiving a tissue, a detection unit configured to detect a unique code identifying the tissue, a measuring unit configured to automatically measure quantitative properties of the tissue, and a processing and storage unit to automatically link the quantitative properties with the tissue code and to automatically store properties and code in order to recover the properties according to the code.

The aforementioned systems and methods of the prior art do not address or overcome problems linked to the correct choice of the container for tissue sample, to the transfer of the tissue sample either fresh or immersed in a preservative substance in a container not yet sealed, to the optimal amount of preservative substance to be used and to the insertion of the same in the container for tissue sample.

In fact, during the transfer of the container not yet sealed from the surgery room to the packing site or to the laboratory, accidental openings can occur with spills in the surrounding environment and damage to the sample.

If the preservative substance is a fixative-preservative solution, in case an under-sized container is chosen, the amount of fixative-preservative solution may not be sufficient to adequately fix the tissue. Consequently, the operator would be forced to decant the tissue sample to be analyzed into a new container with a quantity of fixative-preservative solution suitable for achieving the complete fixation of the tissue to be analyzed; this drawback, in addition to interfering with the workflow, would in-evitably cause delays in the completion of the analysis of the tissue sample and probably would favor the degradation processes of the sample.

SUMMARY OF INVENTION

An object of the present invention is to provide an in vitro diagnostic system having as application, preservation and transfer of tissue or parts of human or animal organs to be subjected to histopathological examinations of histo- and cito-morphological, immunohistochemical and molecular type.

In particular, an object of the invention is to provide a packing machine for the in-troduction into a disposable container of a preservative substance, in particular a fixative-preservative solution, in total safety for the health workers and for the sample of tissue taken.

Another object is to provide a disposable container that can allow to contain an explanted sample in a first packing step directly inside the surgery room without the risk of falling, and to fill the disposable container in a second packing step, with a preservative substance not likely to be dispersed in the environment, not even as a gascous substance.

Yet another object of the present invention is to provide a method characterized by simplicity of use capable of avoiding risks of exposure, both by contact and inhalation, when the preservative substance is a fixative-preservative solution typically containing formaldehyde and/or other toxic or harmful substances.

These and other objects are achieved, in a first aspect of the invention, by a system for preserving a surgically explanted tissue sample as described in claim 1 and in the claims dependent from it, and in a second aspect of the invention by a relative method described in claim 7.

BRIEF DESCRIPTION OF DRAWINGS

Further features and advantages of the invention will become most evident from the description of embodiments of a system of preserving a surgically explanted tissue sample, as illustrated by way of example in the attached drawings, in which.

DESCRIPTION OF EMBODIMENTS OF THE INVENTION

Figure 1:
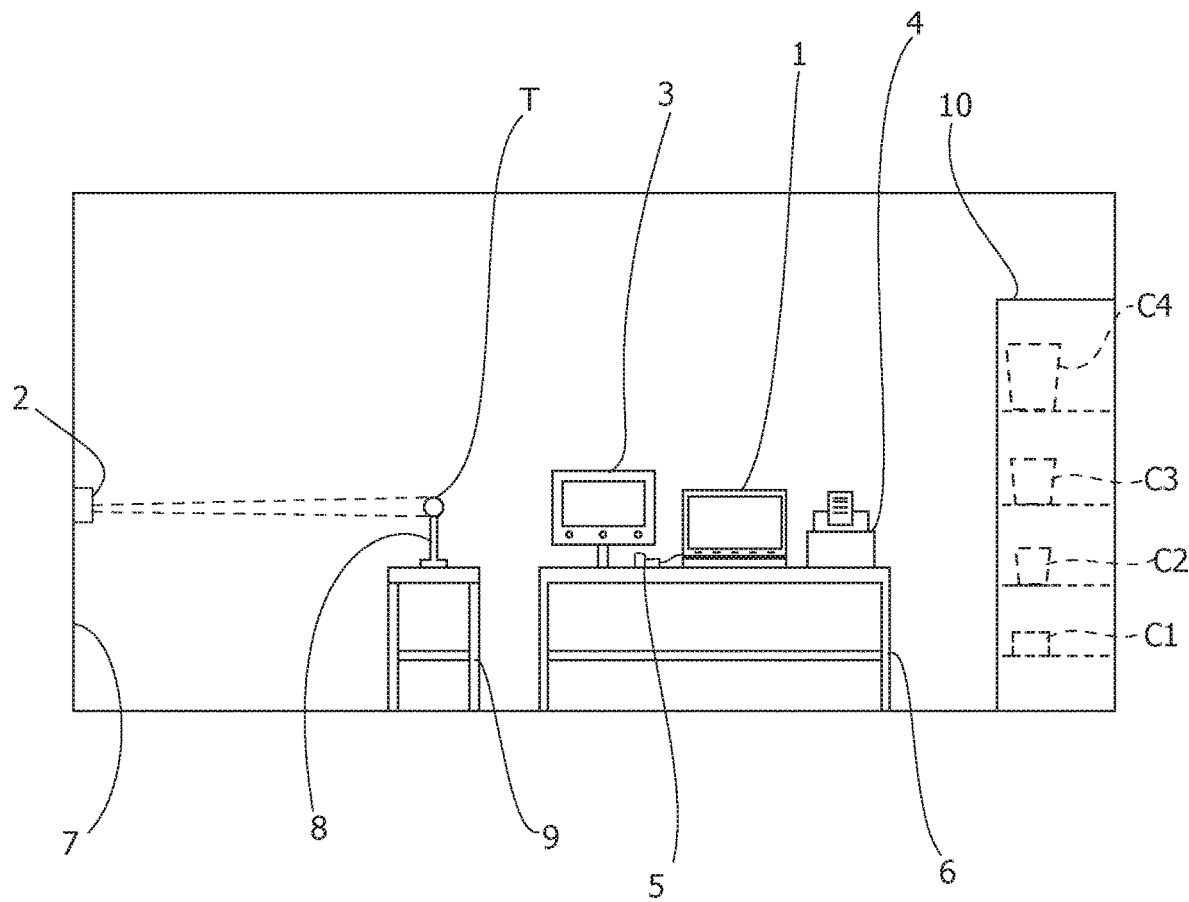
FIG. 1 is a schematic front view of a first packing station for packing the tissue sample.

Reference is initially made to FIG. 1 which is a schematic front view of a station for first packing of the tissue sample. The first packing station is located in a surgery room. The first packing station comprises an electronic control computer 1, a volumetric sensor 2 for measuring the volume of the tissue T or another organ surgically explanted, an electronic device 3 in which a software for selecting a container is installed, a first printer 4, a first bar code reader 5 or the like. These last components of the first packing station are positioned on a table 6, while the volumetric sensor 2 is shown fixed to a wall 7. However, the volumetric sensor 2, even if not shown, could be of a portable or table type. The tissue T for which the volume must be evaluated is supported by a support 8 on a pedestal 9. As an alternative to the electronic control computer 1 and to the electronic device 3 in which the software for selecting the container is installed, a laptop could be sufficient both for the management of the first reader 5 and for data processing and label generation, or first labeling. Furthermore, instead of the volumetric sensor, a balance or other gravimetric device could be used; a table for comparing the specific weight of the tissues present in the software can allow us to evaluate the volume of the explanted tissue.

Next to the table 6, there is a cabinet 10 having shelves on which containers C1, C2, C3, and C4 of various sizes rest. The containers C1, C2, C3, and C4 are provided with own bar code.

Figure 2:
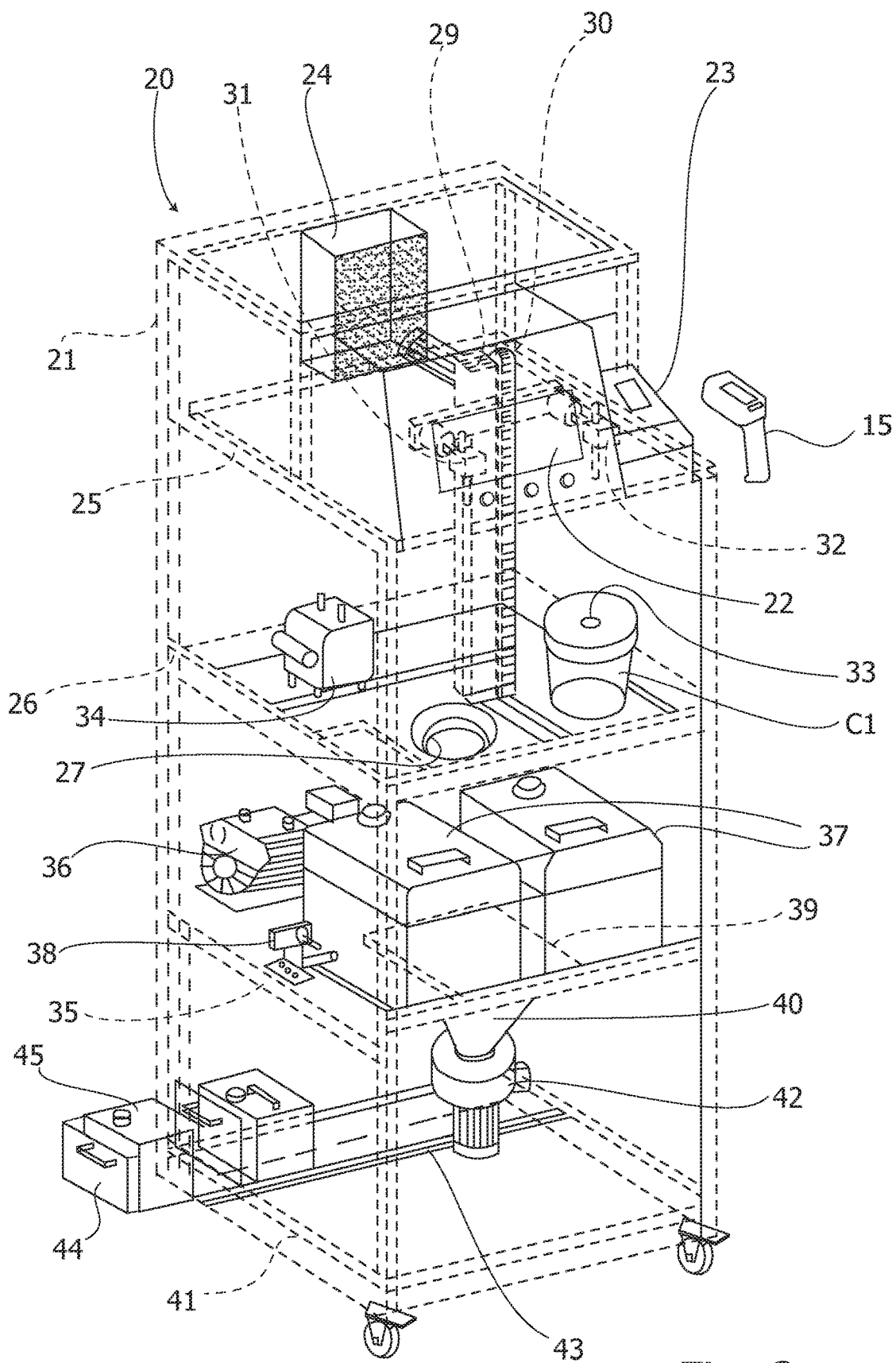
FIG. 2 is a schematic perspective view of a first embodiment of the tissue container packing machine in a final tissue sample packing station, the structure of the machine being shown in transparency.
Figure 3:
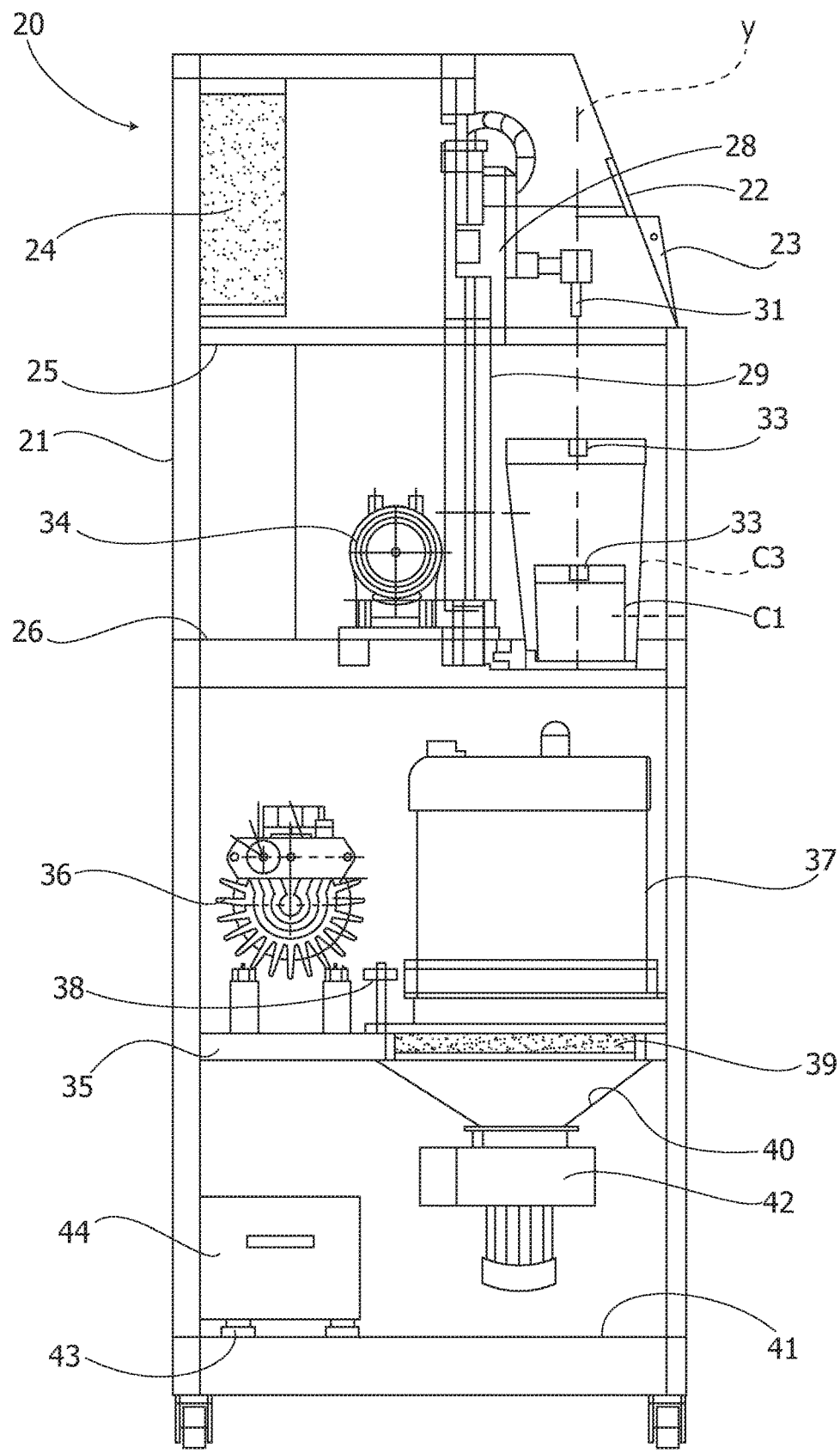
FIG. 3 is a schematic side view of the packing machine in FIG. 2.

Refer now to FIGS. 2 and 3 which are a schematic perspective view and a side view of a first embodiment of the packing machine for packing a tissue container. The packing machine, generally designated as 20, is located in a final tissue sample packing station, generally at a short distance from the first packing station. On a structure 21, which for reasons of clarity is shown in FIG. 2 with a dashed line, the following components are positioned on a first shelf 25 starting from the top: an electronic control panel 22 or touch-screen, a second printer 23, and an inlet dust filter 24.

Formed on a second shelf 26 are recesses 27, which are shaped like the base of tissue containers such as those indicated by C1 and C3 in FIGS. 2 and 3. A filling system, which firstly is supposed a filling system with fixative-preservative solution, comprises a nozzle-holding head 28 mounted movable on a vertical guide 29 thanks to a belt 30. The nozzle-holding head 28 preferably has two nozzles 31, 32 positioned so as to reach, with the lowering along a y-axis (FIG. 3) of the nozzle-holding head 28, an opening 33 of the containers C1, C3. For simplicity, the means for lowering and raising the nozzle-holding head 28 are not shown in greater detail. Shown in the same second shelf 26 of the structure 21 is a pump 34 for dosing a routine fixative-preservative solution, forming part of the filling system. Preferably, a pump is provided for dosing a non-routine fixative for each tank, that is for special uses, not shown in the drawing. Provided on a third shelf 35 starting from the top are a vacuum pump 36, at least one canister 37 containing routine fixative-preservative solution, and a level sensor 38 of the fixative-preservative solution for each canister 37. On the same third shelf 35 there is a filter 39 specific for the abatement of formaldehyde, which preferably but not exclusively uses graphene or activated carbon and a suction cup 40. In the fourth shelf 41, the lowest of the structure 21, an air suction fan is provided with biohazard absolute filter 42 and on a guide 43 a drawer 44 with external connection to a disposable canister 45 with anti-drip quick coupling. The disposable canister 45 is used to contain a fixative-preservative solution not of routine use, that is to say for special uses.

Through the fan for the intake of air with an absolute biohazard inlet filter 42, the air is filtered through the inlet dust filter 24 and conveyed out through the filter 39. Furthermore, the filter 39 ensures a total absorption of any toxic-harmful vapors of fixative-preservative solutions in the event of accidental events inside the packing machine, in which there is an alarm system in case of formaldehyde exit. The air leaving the packing machine through a tube not shown in the drawings can be conveyed to a gas expulsion system from a surgery division.

Figure 4:
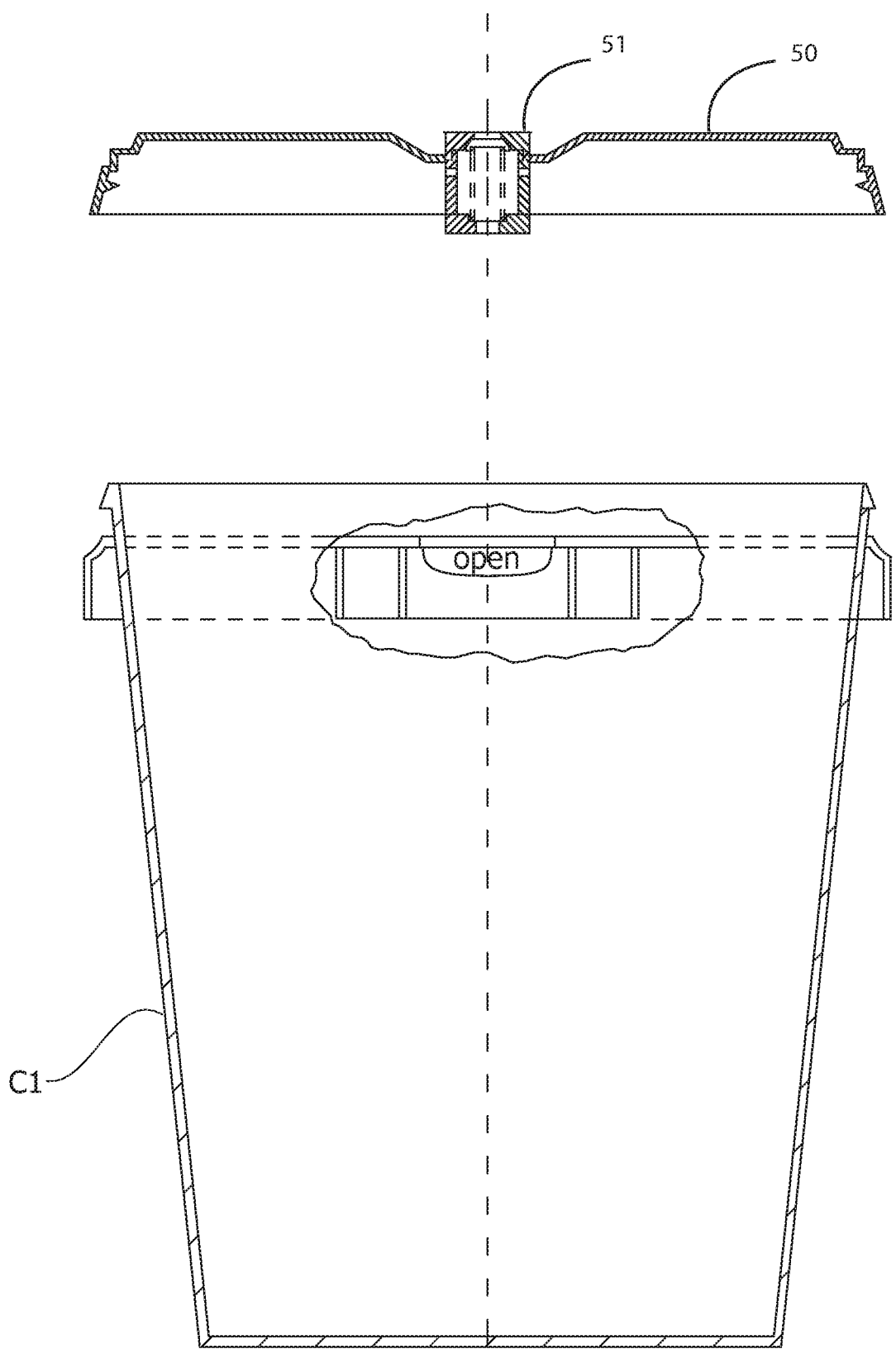
FIG. 4 is a schematic central vertical cross-section, partially in view, of the tissue container with the lid removed.

Reference is made now to FIG. 4 which is a schematic central vertical cross-section, partially in view, of a tissue container C1 with its lid being removed. The lid is indicated as 50. The container C1 is a conventional frustoconical container made of plastic material; however, the container could be of a different shape, for example cylindrical or prismatic. The lid 50 is snap-fit onto the top of the container. However, it does not require a detailed description except for its feature of presenting, prefer-entially but not exclusively in a central position, an opening closed with a non-return valve 51. The non-return valve 51 is more visible in FIG. 7 which is a schematic side view, partially in section, of a detail of the machine and of the container, which will be shown in greater detail below.

Figure 5:
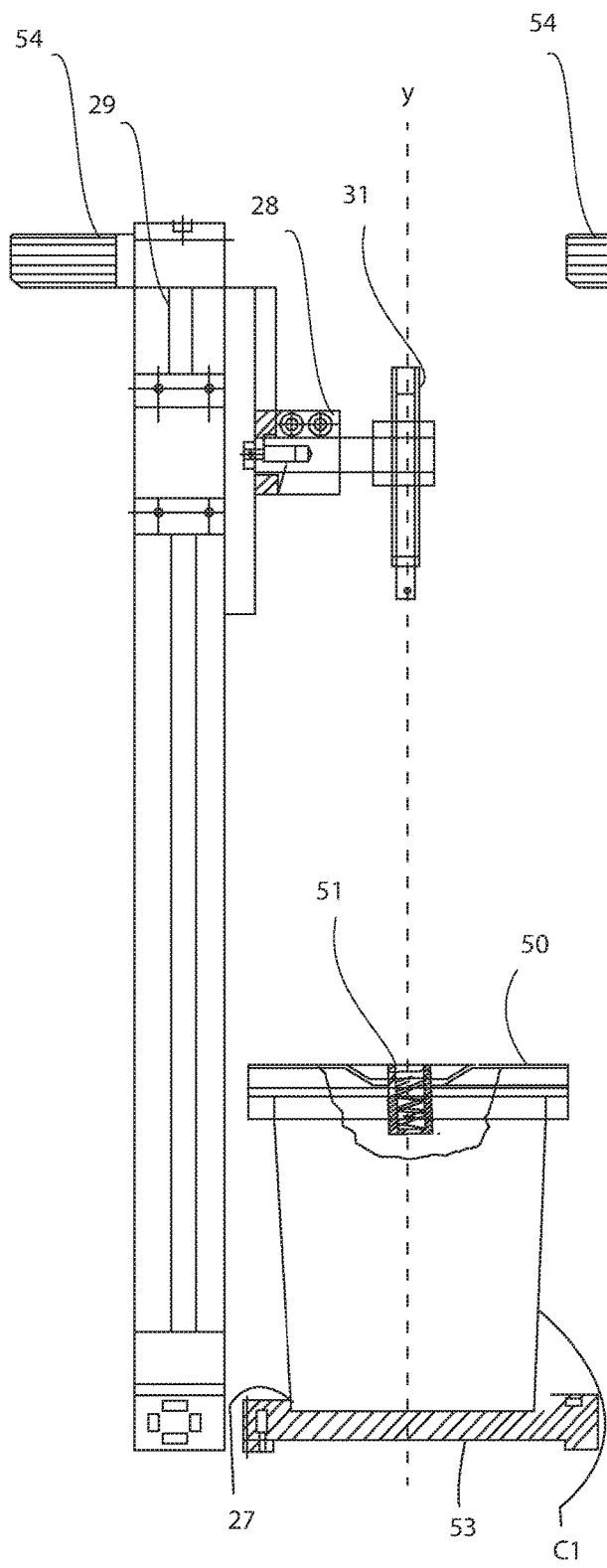
FIGS. 5 and 6 are partial schematic side views of the packing machine and of the tissue container in successive operating steps.
Figure 6:
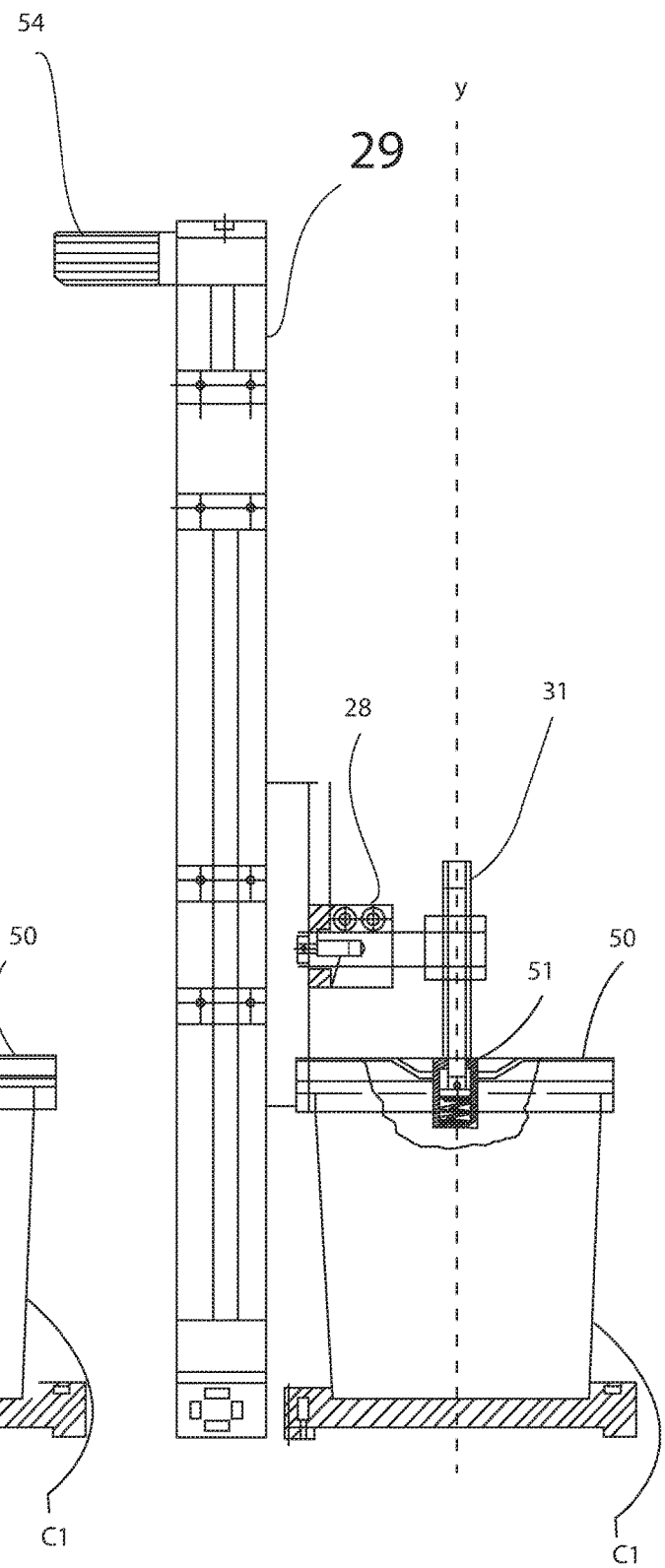

Referring to FIGS. 5 and 6 which are partial schematic side views of the packing machine and the tissue container C1, two successive operating steps are shown. FIG. 5 shows the nozzle-holding head 28 in its highest position above a container C1 positioned in the recess 27 in a base 53 of the second shelf 26. The container C1 is closed with a lid 50 whose upper opening, equipped with a non-return valve 51 is coaxially arranged along the axis y at the nozzle 31. FIG. 6 shows that the head 28 has been lowered along the vertical guide 29 thanks to a motor 54 with displacement means not described in detail. In this position, the nozzle 31 is her-metically sealed inside the non-return valve 51 to allow a safe dispensing of the fixative-preservative solution.

Figure 7:
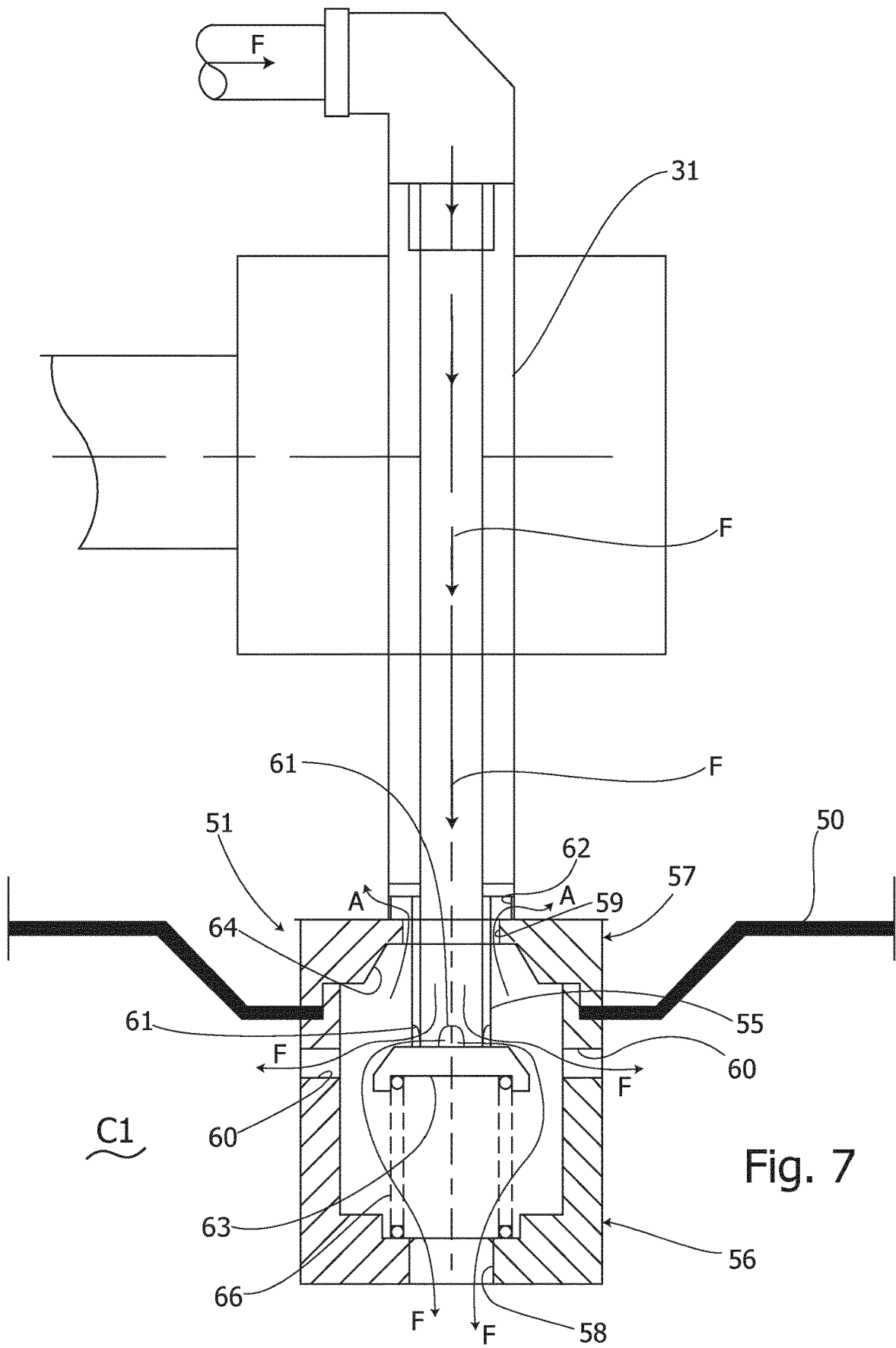
FIG. 7 is a schematic side view, partially in section, of a detail of the machine and the container.

Reference is now made to FIG. 7 which is a schematic side view, partially in section, of a detail of the machine and of the container arranged coaxially. As shown, the nozzle 31 is inserted with its free end 55 in the non-return valve 51.

As can be seen in the schematic representation, the non-return valve 51 has a lower part 56 positioned below the lid 50 and an upper part 57 joined to the lower part 56 and positioned above the lid 50. Both the lower part 56 and the upper part 57 have coaxial holes, indicated as 58 and 59 respectively. Furthermore, the lower part 56 has side openings indicated as 60.

The nozzle 31 is inserted with its end 55 through the hole 59. The end 55 has a distal part with lateral openings indicated generically as 61 and proximal passageways indicated as 62. After insertion, the lateral openings 61 are delimited inferiorly from a valve cap 63, loaded by means of a spiral spring 66, abutted at its other end to the bottom of the lower part 56 of the non-return valve 51. In fact, the free end 55 of the nozzle 31 presses on the valve cap 63 which normally closes the non-return valve 51, when at rest the valve cap 63 positions itself in a recess 64 of the upper part 57 of the non-return valve 51 to allow its operation.

When the free end 55 has moved the cap 61 downwards, the fixative-preservative solution can be fed in order to escape from the nozzle 31 according to the arrows F through the hole 58 and the openings 60 of the lower part 56 of the non-return valve 51. In this way, the fixative-preservative solution is introduced into the container C1. The fixative-preservative solution containing formaldehyde is shown advancing according to the arrows F along the nozzle 31, while the air is free to escape according to the arrows A through the hole 59 of the upper part 57 of the non-return valve 51 at the proximal part of the free end 55. Both the nozzle 31 and the nozzle 32 in FIG. 2 can be intended for filling containers, as shown in FIG. 7.

Figure 8:
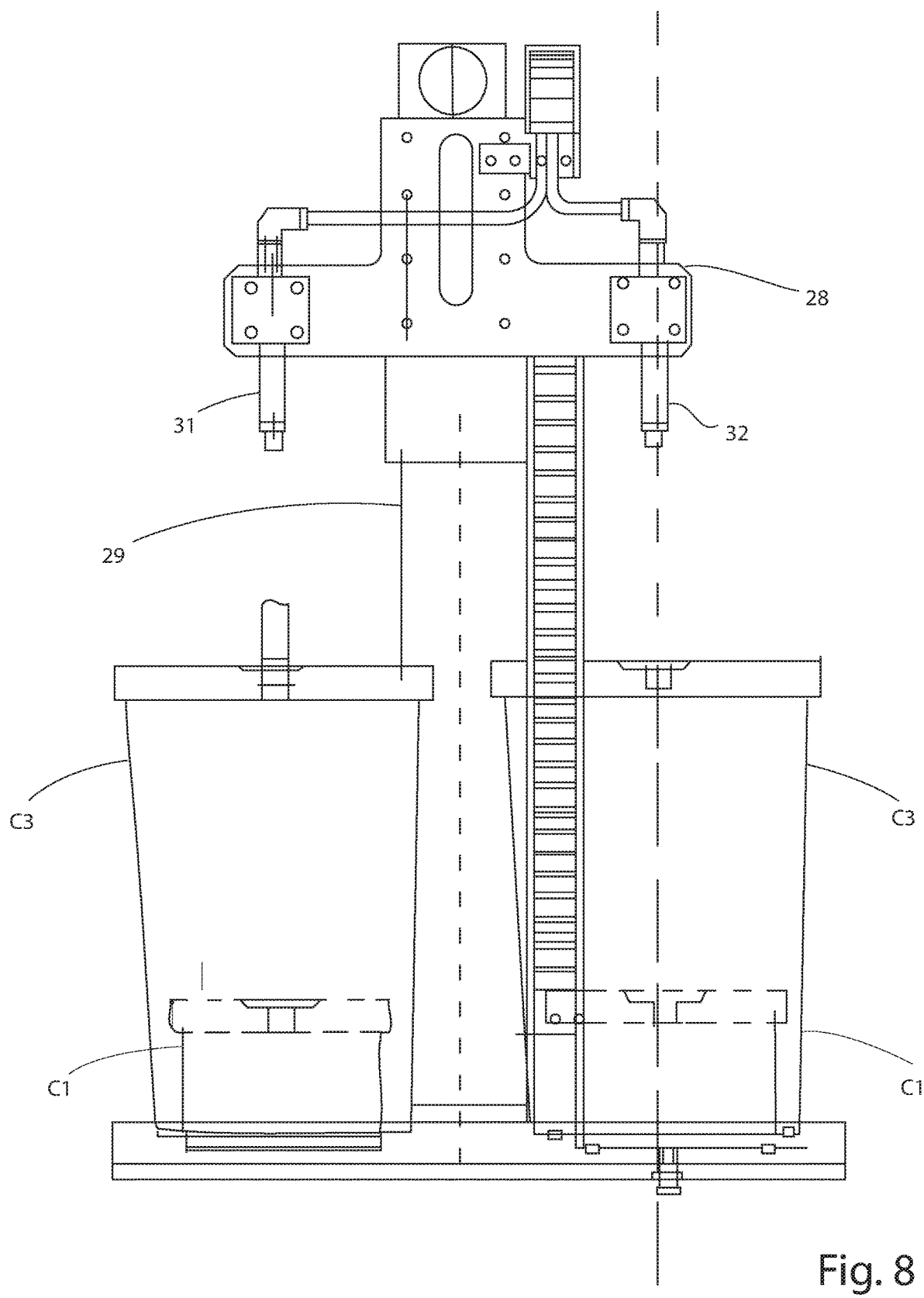
FIG. 8 is an enlarged partial front view of the packing machine.

Air exiting the non-return valve 51 could contain form-aldehyde vapors. As shown in FIG. 8, which is an enlarged partial front view of the packing machine, it is possible to create, before filling with the fixative-preservative solution, a low pressure inside the container C3 by partial aspiration of the air contained therein through the nozzle 32 that is connected to a suction pump non shown.

Figure 9:
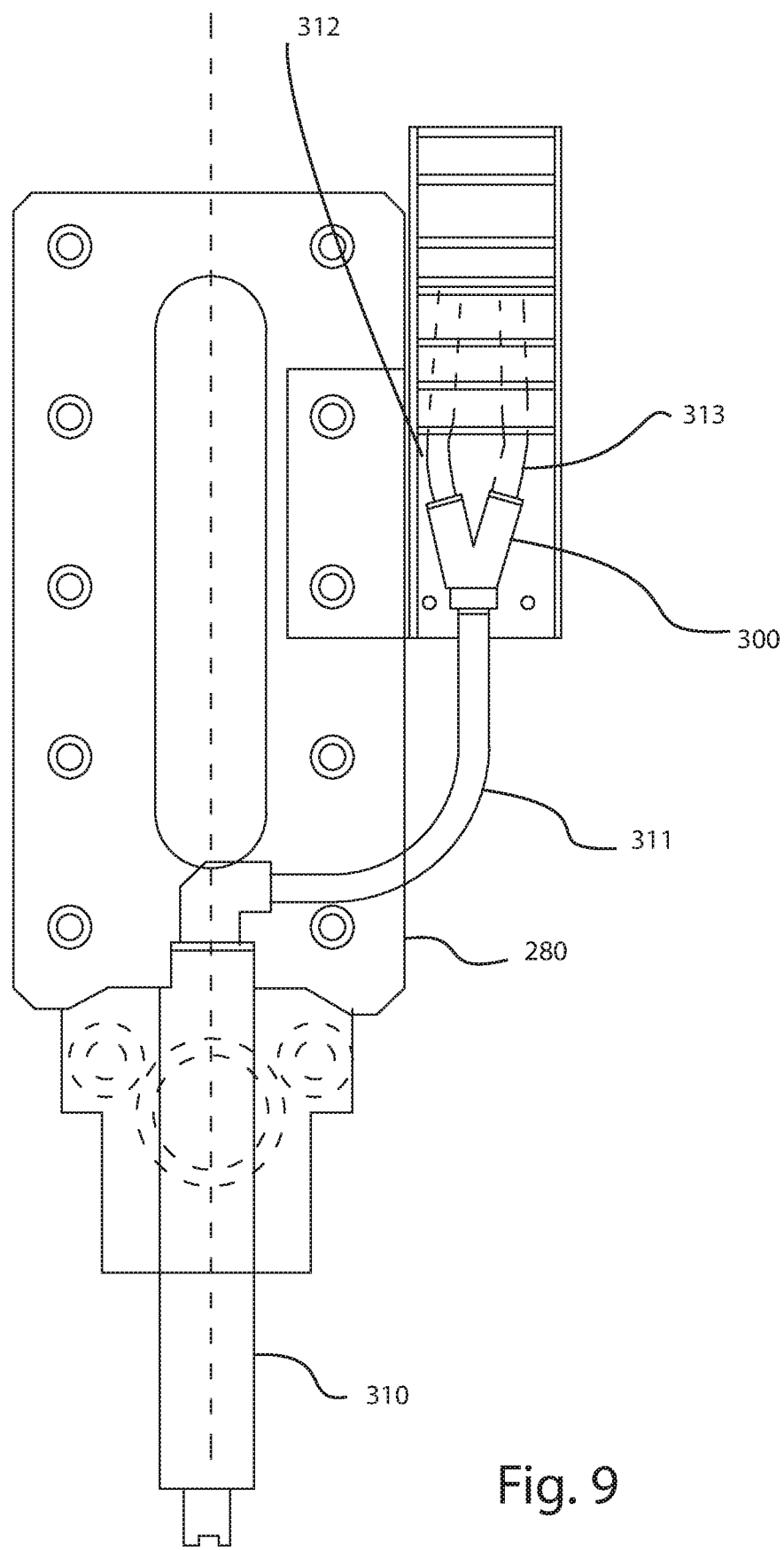
FIG. 9 is a front view of a detail according to an alternative embodiment of the machine.

Reference is made now to FIG. 9 which is a front view of a detail according to an alternative embodiment of the machine according to the present invention.

It shows a nozzle-holding head 280 holding a nozzle 310. Unlike what has been described for the nozzle-holding head 28, the nozzle 310 is connected by means of a hose 311 to a V-shaped coupling 300. The V-shaped coupling 300 serves as a connection to a feeding tube 312 for supplying the fixative-preservative solution, and to an air tube 313 connected to the pump functioning as a compressor to supply air and drip a nozzle into the container C1 or C3 or different before extracting said nozzle from the lid 50.

Alternatively, the embodiment shown in FIG. 9 can be used for preserving a tissue sample with an inert gas, such as for example nitrogen, or a mixture of inert gases, under controlled temperature conditions. Since this procedure requires the evacuation of the air from inside the container C1 or C3 before the subsequent insertion of the inert gas therein, the nozzle 310, which is connected by means of the hose 311 to the V-shaped coupling 300, carries out first the suction of air from inside the container through the tube 313 connected to the pump operating as an suction pump and then supplies the container C1 or C3 with inert gas through the hose 312. The inert gas is produced with any known type device which replaces the provision of the canisters and all that is not necessary of the devices described above for using the inert gas. As an example, filters will not be necessary that are not required when a preservative is not used that is harmful and dangerous for operators.

The method for preserving a tissue sample according to the present invention in its embodiment using a fixative-preserving solution is now described.

The operator working for the fixation of a tissue sample in the surgery room uses the volumetric sensor 2 (FIG. 1) to measure the volume of the tissue or organ or its parts that are surgically explanted. The control electronic computer 1 automatically prescribes the volume of the container C1, C2, C3 or C4 to be used for storing the tissue and for delivering the right amount of fixative-preservative solution necessary for a correct fixation. The containers C1, C2, C3, and C4 are provided with own bar code. From the fixation depends a good result of a histological preparation since it allows to maintain unchanged structurally and morphologically of the tissues. Then, the operator takes the prescribed container from the cabinet 10 and positions the first code reader 5 on the bar code of the container to verify the correct identification; below, he/she inserts patient's data and all necessary information in compliance with current guidelines and procedures implemented in the clinical center. With a drop-down menu the operator selects the department of origin and the organ or part thereof to be treated. The electronic device 3 on which the software is installed helps the operator in choosing the relevant program, which consists in the use of the routine fixative-preservative solution, or of the fixative-preservative solution for special uses and in applying or not a low pressure inside the container, so-called partial vacuum.

Once the surgically explanted tissue sample has been inserted in the suitable container, this is closed with a lid 50, to which a safety seal can be affixed.

The first printer 4 automatically generates a bar code label identifying all the patient's data and the program selected for the correct packing of the surgically explanted tissue sample. The label is attached to the chosen container. Alternatively, in order not to burden the label with too much information, transmission of a data file, including the patient's data and the program selected for correct packing, can be performed via Local Area Network to the final packing machine.

Steps performed by the operator in the surgery room take place in an aseptic environment that excludes bacterial contamination of the air inside the container.

The tissue sample disposable containers are of two types, the one for the insertion of fixative-preservative solutions, the other that provides for the creation of a low pressure within them. Obviously, the second type of containers has a better resistance to the collapse that could be caused by the creation of the partial vacuum inside the container. A low pressure obtained by extracting an amount of air equal to 30%-40% of the volume of the disposable container is sufficient.

The method according to the present invention continues with the transfer of the container to the final packing machine shown in FIGS. 2 and 3; this machine is typically, but not exclusively, arranged in a "dirty area" of the surgery division.

An operator for the final packing uses a second code reader 15 to read the identification bar code with all the patient's data on the container, including the program chosen for that packing type of the tissue sample surgically explanted. The operator opens a machine door (not shown) and inserts the container in the second shelf 26 at the recess 27 in the base 53. Then, the machine door closes, and the final packing machine is ready to execute the required program. The machine door hermetically closes the final packing machine to avoid the spread of formaldehyde vapors in the cn-vironment, if the chosen program involves the insertion of the fixative-preservative solution.

In this case, the packing machine automatically doses the correct quantity of routine fixative-preservative solution necessary for the correct fixation of the tissue sample taken according to the procedures implemented in the single center. In fact, the amount of fixative-preservative solution may vary from center to center. Thanks to the possible presence of two canisters for routine fixative-preservative solution, upon emptying the first canister, the solution can be supplied from the second canister connected.

If the chosen program involves the insertion of the fixative-preservative solution for special uses, the machine automatically checks for the presence of the fixative canister 45 for special uses inside the lateral drawer 44. In the absence of the suitable canister, this is signaled on the electronic control panel and the operator will replace it with the correct one simply by unhooking the anti-drip quick coupling and inserting it in the other, then going to identify the canister by reading the bar code on the canister itself. Subsequently, the operator opens the lateral drawer 44 slidable on the guide 43 and actuates the valve placed on the anti-drip quick coupling of the canister 45 for the dosage of the fixative-preservative solution necessary for the correct fixation of the surgically explanted tissue sample. Instead of canister 45 for special uses, a canister with a normal fixative-preservative can be placed suitable for that sample of tissue to be treated.

At the end of the selected packing programs, the machine door opens in order the container is removed. The second printer 23 processes a second label or second identification label with a bar code with all the patient's data, automatically inserting the date and time of packing. The second label is affixed to the container; this last indication is used by a laboratory to calculate the correct fixation times of the tissue sample or organ or of their parts to be examined for the correct diagnosis.

The subsequent transfer of the disposable container with the tissue sample from the final packing machine to the laboratory takes place without any risk of operator exposure and biological or chemical contamination of the environment thanks to the seal of the non-return valve 51 and to the safety seal on the hermetic lid 50. Once in the laboratory, the disposable container with the tissue sample can be opened and ma-nipulated by the operator safely under the hood.

If the program chosen is that with a fixative-preservative solution, tissue excision will be performed for subsequent analyses; at the end, the tissue sample will be re-entered in its container, which will be closed with the hermetic lid and stored as required by current legislation.

If the program chosen is the one without a fixative-preservative solution, the tissue is excised for fresh analyses; after which the tissue sample will be placed back into the container and filled with the fixative-preservative solution for proper fixation; at the end of the fixation, the tissue to be analysed will again be excised; after this operation, the tissue sample is placed in the closed container with the hermetic lid and stored as required by applicable legislation.

As an alternative to fixation, the tissue sample can be preserved with an inert gas, such as for example nitrogen, or a mixture of inert gases, under controlled temperature conditions. Since this procedure, as previously stated, requires the evacuation of the air from inside the container C1 or C3 before the subsequent insertion of the inert gas therein, the nozzle 310 first performs the suction of air from the inside of the container through the tube 313 connected to the suction pump and then supplies the container C1 or C3 with the inert gas through the hose 312.

The invention claimed is:

1. A system for preserving a surgically explanted tissue sample, comprising:
   a first packing station for placing the tissue sample in a selected container among a plurality of containers (C1, C2, C3, C4) of different sizes, the first packing station including a control electronic processor (1), a volumetric sensor (2) for the measurement of the volume of the tissue (T) or another organ surgically explanted, a first printer (4), a first bar code reader (5), a cabinet (10) on whose shelves are the containers (C1, C2, C3, C4) of different sizes, provided with hermetic lids (50); and
   a final packing station comprising a filling system for filling the selected container with a preservative substance, the filling system including a nozzle-holding head (28) mounted movable on a vertical guide (29), the nozzle-holder head (28) having at least one nozzle (31) for filling the selected container,
   characterized in that the hermetic lid (50) of the selected container is provided with an opening (33) equipped with a non-return valve (51).

2. The system according to claim 1, wherein the non-return valve (51) comprises:
   a lower part (56) positioned under the lid (50) and containing a spiral spring (66) and a valve cap (63), the lower part (56) having a hole (58) on the bottom and side openings (60), and
   an upper part (57) joined to the lower part (56) and positioned above the lid (50), the upper part (57) being provided with a hole (59) concentric with the hole (58) of the lower part (56) in a recess (64) intended to be closed by the valve cap (63).

3. The system according to claim 2, in which the nozzle (31) has an end (55) intended to be inserted in the hole (59) of the upper part (57) of the non-return valve (51) against the valve cap (63) charged by the spiral spring (66), the end (55)

having a distal part with lateral openings (61) and proximal passages (62) for the exit of the preserving substance when the nozzle (31) is inserted into the non-return valve (51).

4. The system according to claim 1, wherein the first packing station further comprises an electronic device (3) in which a software for the selection of the container (C1, C2, C3, C4) based on the volume of the of explanted tissue sample is installed.

5. The system according to claim 4, wherein the volume of the explanted tissue sample is supplied to the software by the volumetric sensor (2).

6. The system according to claim 4, wherein the first packing station comprises a weighing scale for the explanted tissue sample and a comparative weight and volume table for each type of tissue explanted in the software for selecting a container (C1, C2, C3, C4) on the basis of the volume of the explanted tissue sample.

7. The system according to claim 1, wherein the preservative substance is a fixative-preservative solution.

8. The system according to claim 7, wherein the fixative-preservative solution is based on formaldehyde.

9. The system according to claim 1, wherein the preservative substance is a mixture of inert gases.

10. The system according to claim 1, wherein the preservative substance is an inert gas.

11. A method of preserving a sample of surgically explanted tissue, comprising the following steps:
   selection of a container suitable for preserving the tissue sample between a plurality of containers (C1, C2, C3, C4) of different sizes,
   calculation of the quantity of preservative substance necessary for preserving the tissue sample based on its mass,
   first labeling of the container for its recognition,
   transfer of the selected container to a final packing station,
   insertion of the tissue sample into the selected container,
   filling of the selected container with the calculated quantity of preservative substance, and second labeling of the container for the calculation of the correct times for preserving the tissue sample to be examined for diagnosis, characterized in that
   the selection of the container is made on the basis of the evaluation of the volume of the tissue sample;
   a hermetic closure of the selected container is performed immediately after inserting the tissue sample into the selected container equipped with a hermetic lid (50) with non-return valve (51); and
   the filling of the container with a fixative-preservative solution takes place by means of a nozzle (31) of a filling system inserted in the non-return valve (51) of the hermetic lid (50) of the selected container.

12. The method according to claim 11, wherein the preservative substance is a fixative-preservative solution.

13. The method according to claim 12, wherein the fixative-preservative solution is based on formaldehyde.

14. The method according to claim 11, wherein the preservative substance is a mixture of inert gases.

15. The method according to claim 11, wherein the preservative substance is an inert gas.

* * * * *